United States Patent [19]

Butte, Jr. et al.

[11] 4,186,146

[45] Jan. 29, 1980

[54] HYDROGENATION OF AROMATIC NITRILES TO PRIMARY AMINES

[75] Inventors: Walter A. Butte, Jr., West Chester; William J. Murtaugh, Eddystone, both of Pa.

[73] Assignee: Suntech, Inc., Philadelphia, Pa.

[21] Appl. No.: 8,310

[22] Filed: Feb. 1, 1979

[51] Int. Cl.$^2$ .............................................. C07C 85/12
[52] U.S. Cl. ........................... 260/570.5 P; 260/570.9
[58] Field of Search ....................... 260/570.5 P, 570.9

[56] References Cited

U.S. PATENT DOCUMENTS

| | | | |
|---|---|---|---|
| 3,069,469 | 12/1962 | Wilkes | 260/570.9 |
| 3,255,248 | 6/1966 | Seemengoth et al. | 260/570.5 P X |
| 3,372,195 | 3/1968 | Dile | 260/570.9 |
| 3,720,702 | 3/1973 | Nelson et al. | 260/570.9 X |
| 3,923,891 | 12/1975 | Greenfield at al. | 260/570.9 |
| 4,003,933 | 1/1977 | Drake | 260/570.5 P X |
| 4,140,720 | 2/1979 | Drake | 260/570.9 X |

FOREIGN PATENT DOCUMENTS

| | | | |
|---|---|---|---|
| 536940 | 6/1941 | United Kingdom | 260/570.9 |
| 810530 | 3/1959 | United Kingdom | 260/570.9 |
| 1149251 | 4/1969 | United Kingdom | 260/570.5 P |

OTHER PUBLICATIONS

Rupe et al., "Helv. Chem. Acta.", 6, pp. 865–880 (1923).

*Primary Examiner*—John Doll
*Attorney, Agent, or Firm*—J. Edward Hess; Donald R. Johnson; Paul Lipsitz

[57] ABSTRACT

In the process of hydrogenating aromatic nitriles to primary amines whereby the nitrile is hydrogenated in a solvent system containing added ammonia using a cobalt or nickel catalyst, the improvement of employing an ether as solvent and carrying out the hydrogenation in the presence of water in an amount of from about 10% to about 20% by volume of the ether solvent whereby the rate of reaction is increased, secondary amine by-products are reduced and catalyst may be recycled without adverse effects.

9 Claims, 3 Drawing Figures

HYDROGENATION OF AROMATIC NITRILES TO PRIMARY AMINES

CROSS REFERENCES TO RELATED APPLICATIONS

This application is related to the following applications filed of even date herewith:

Walter A. Butte, Jr. and Howard P. Angstadt entitled "Hydrogenation of Aromatic Amines", Ser. No. 8309.

Walter A. Butte, Jr., William J. Murtaugh and Richard E. Mitchell, and Howard P. Angstadt, entitled "Process For Hydrogenating Aromatic Dinitriles", Ser. No. 8313.

Walter A. Butte, Jr., William J. Murtaugh and Richard E. Mitchell, entitled "Hydrogenation of Aliphatic Nitriles To Primary Amines, Ser. No. 8315.

It is known in the art to effect hydrogenation of aliphatic and aromatic nitriles to the corresponding amines in the presence of various catalytic materials. For example, U.S. Pat. No. 3,069,469 discloses the hydrogenation of aromatic nitriles with a combined cobalt and nickel catalyst where the nitrile, hydrogen, ammonia, and solvent (such as the isomeric xylenes, dioxane, and aliphatic alcohols) are brought into contact with the catalyst. A combined cobalt-nickel catalyst is employed in order to reduce the amount of undesirable hydrogenolysis of the desired product. This hydrogenolysis leads to secondary amines which contaminate the desired primary amine products and this phenomenon is common in nitrile hydrogenation. Another disclosure of interest is U.S. Pat. No. 3,252,248 which details the catalytic hydrogenation or organic nitrogen-containing carbon compounds (including aliphatic and aromatic nitriles) to amines in a liquid phase system using a specifically prepared sintered catalyst of cobalt or nickel. Because such specially prepared catalysts are said to be of high mechanical strength they are suitable when used in a method in which the initial material, either alone or in admixture with a solvent such as water, tetrahydrofuran, ammonia, methanol or the reaction product formed, is trickled together with hydrogen over the catalyst in a reaction tube. In Example 1 of this patent, an aliphatic nitrile (aminoacetonitrile) is hydrogenated in a mixture of liquid ammonia and an aqueous aminonitrile solution (about 6.6% of the total liquid reactants being water) in the presence of the specially prepared sintered catalyst to obtain ethylenediamine. In Example 11 where isophthalodinitrile is the starting material a non-aqueous system is employed.

A process for hydrogenation of aromatic dinitriles to the corresponding diamines is also disclosed in United Kingdom Patent Specification No. 1,149,251. In this disclosure the dinitrile is hydrogenated with a zirconium promoted cobalt catalyst in the presence of ammonia using a solvent system such as aliphatic or aromatic hydrocarbons, aliphatic alcohols, dimethylformamide and dioxane. Example 3 of this disclosure illustrates hydrogenation of isophthalonitrile in a methanol-water mixture, but the amounts of the solvent components is not given.

Also of interest is the publication of H. Rupe and E. Hodel in Helv. Chem. Acta 6 865–880 (1923) which points out that in the hydrogenation of nitriles with a nickel catalyst in an aqueous system at atmospheric pressure, the water reacts with intermediates to form significant aldehydes which, in turn leads to secondary amines being present in the reaction product. A later publication (U.S. Pat. No. 3,372,195, 1968) confirms that water is detrimental in reducing nitriles to primary amines. In U.S. Pat. No. 3,372,195 it is reported that numerous types of nitriles including aliphatic and aromatic nitriles and cyanoethylated glycols may be converted to the corresponding primary amines by hydrogen reduction under pressure with a ruthenium catalyst and in the presence of ammonia using as a solvent system any one of a number of solvents including water. However, the disclosure adds that with nitriles having a molecular weight lower than about 200, water is not preferred due to its tendency to cause increased by-product formation.

It has now been found in the hydrogenation to primary amines of aromatic nitriles, particularly aromatic nitriles of the benzene and naphthalene series, in the presence of ammonia and using a cobalt or nickel catalyst, that the presence of a specific amount of water significantly improves the process. One particularly valuable improvement is the increase in reaction rate that is obtained with high yields of product being obtained. Another unexpected advantage, particularly in view of the Rupe et al article and U.S. Pat. No. 3,372,195 mentioned above, is that the formation of unwanted secondary amine by-products is suppressed. Also, the use of water in the hydrogenation reaction of this invention enables the catalyst to be reused repeatedly without adverse effects.

In accord with the process of the invention an aromatic nitrile, preferably of the benzene and naphthalene series, is hydrogenated to a primary amine in a solvent system comprising an ether, ammonia and an amount of water of from about 10% to about 20% by volume of the solvent used.

In carrying out the process of the invention a mixture of the solvent, nitrile, ammonia, water and catalyst is heated to a reaction temperature of from about 85° C. to about 150° C., preferably about 115° C. and hydrogen introduced, with stirring, to a hydrogen pressure of from about 500 to about 3000 psig. The reaction is allowed to proceed until hydrogen uptake ceases or until aliquot samples show that all of the nitrile has been converted. then, the reactor is cooled and vented and the contents are removed and filtered to recover the catalyst. The filtrate is distilled to recover solvent and the product is distilled under reduced pressure.

The process is useful with a wide variety of aromatic nitriles, but will preferably employ those of the benzene or naphthalene series such as benzonitrile, tolunitrile, phthalonitrile, isophthalonitrile, terephthalonitrile, 1- or 2-cyanonaphthalene, 1,2-, 1,4-, 1,6, or 1,10-dicyanonaphthalene and the like. It will be understood that the aromatic ring may have inert substituents such as lower alkyl (methyl, ethyl, butyl, etc.), halogen, alkoxy, and similar groups inert to the hydrogenation.

The solvent used will be an ether or a polyether (di- or tri-preferred) preferably with 4 to 6 carbon atoms and a carbon:oxygen ratio of from 2:1 to 5:1 such as dioxane, tetrahydrofuran, ethylene glycol dimethyl ether and diethyleneglycol dimethyl ether. Cyclic ethers such as dioxane and tetrahydrofuran are most preferred.

The yield of primary amines produced in the process declines as the concentration of nitrile in the solvent is increased. In general, satisfactory results are obtained with up to about 25% nitrile by weight based on solvent. Lower concentrations are preferred but practical considerations will normally dictate about 5% as the lower limit.

The catalyst used will be a conventional nickel or cobalt hydrogenation catalyst and may be skeletal catalyst such as Raney nickel or Raney cobalt or the catalyst may be supported on a support such as alumina, silica, kieselguhr, silica-alumina and the like. Preferably, the supported catalyst will be pre-reduced with hydrogen and will contain 75-95% or cobalt and will have a silica and/or an alumina type binder. The amount of catalyst used is not critical, but will usually be from 1 to about 20 wt. percent of the nitrile in a batch hydrogenation process.

The process can also be carried out in a continuous trickle bed reactor. In that case, the nitrile solution and hydrogen are passed thru a catalyst bed and the catalsyt is present in large excess over the nitrile contained in the reaction zone.

The amount of ammonia in the reaction mass will be from about 10% to about 30% by volume of the solvent. The ammonia is believed to be helpful in supressing the formation of unwanted secondary and tertiray amine by-products.

Figure 1:
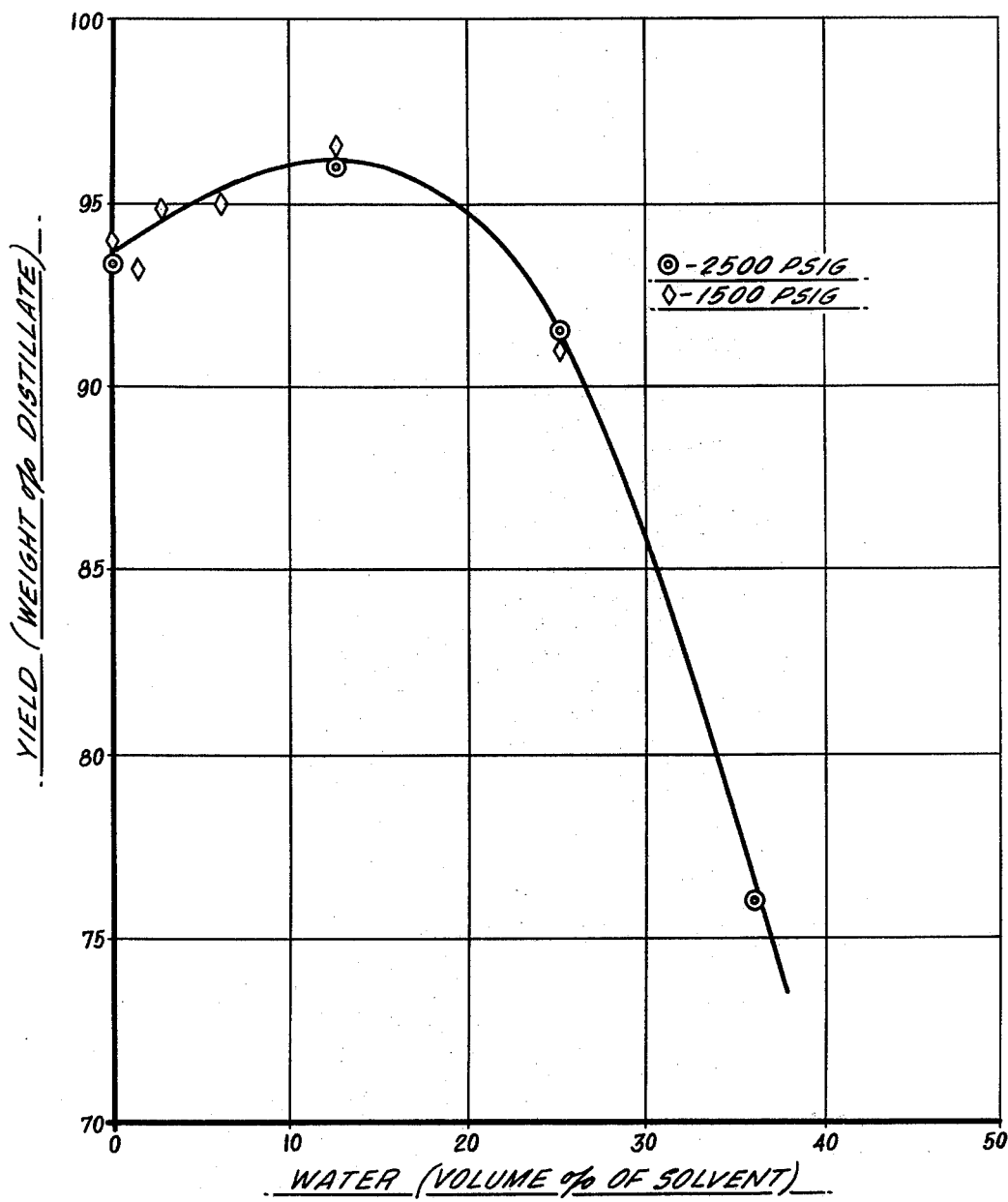
FIG. 1 is a graph showing how the yield of derived product is affected by various amounts of water in the reaction mass.
Figure 2:
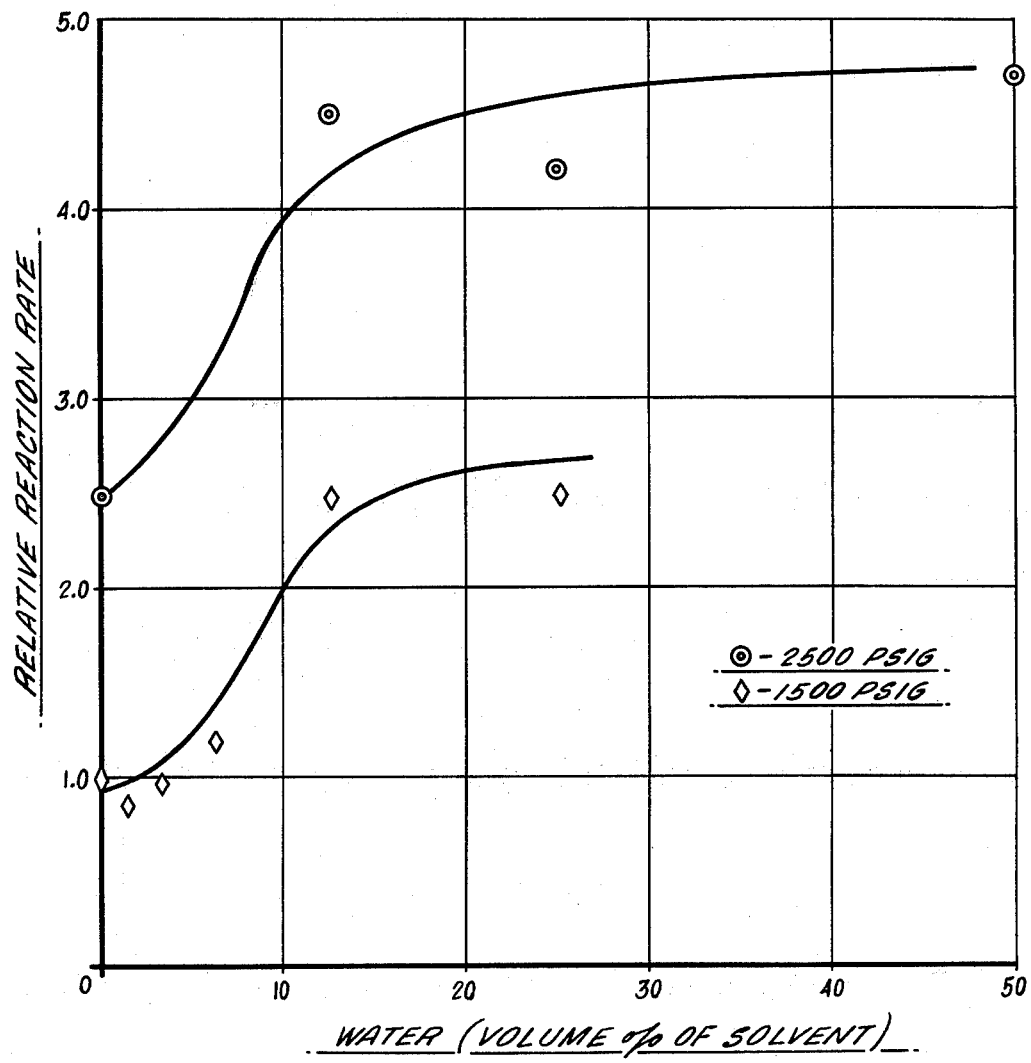
FIG. 2 shows the rate of reaction versus water concentration.
Figure 3:
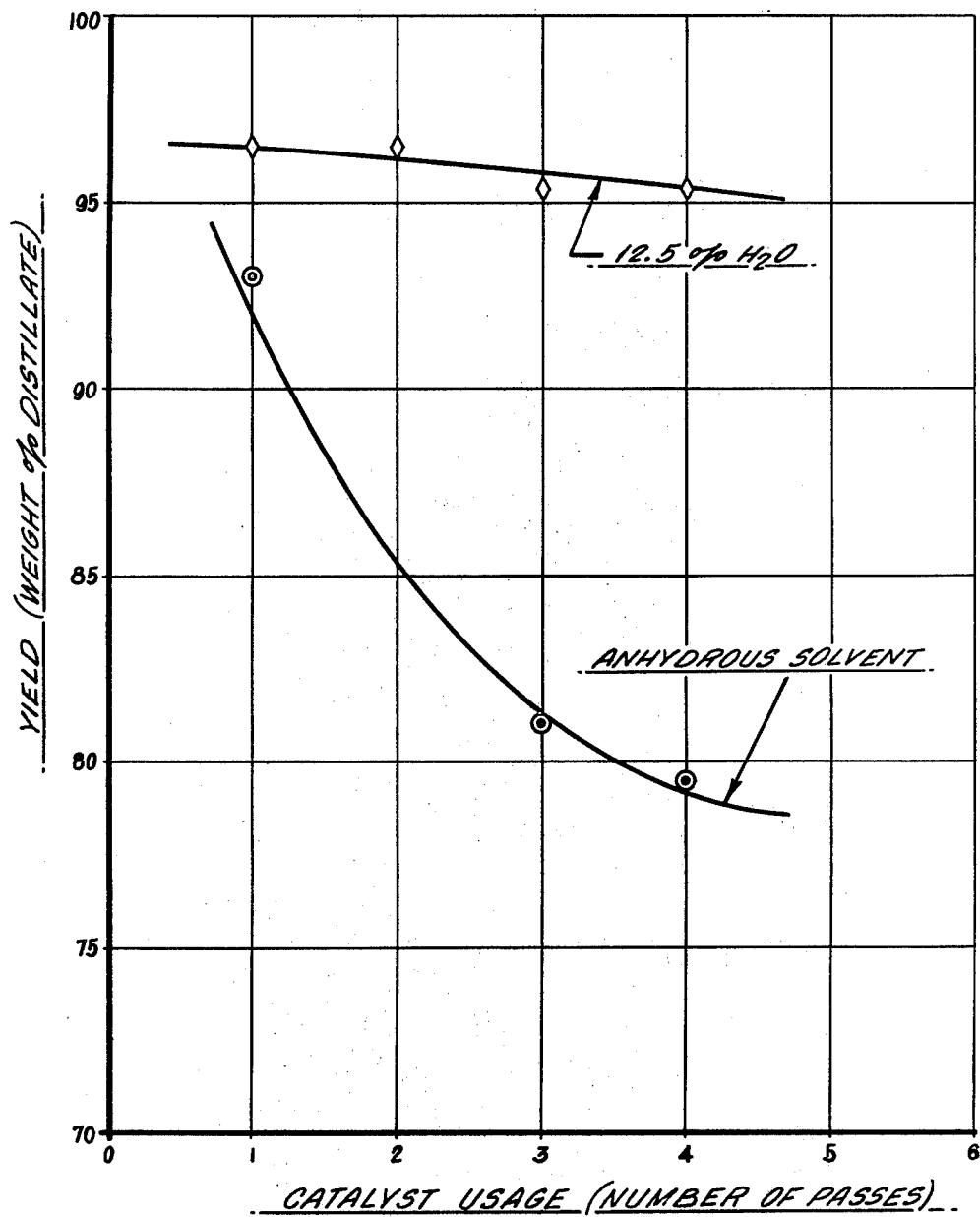
FIG. 3 shows how the catalyst may be recycled in the process of the invention.

The presence of a specific amount of water in the reaction mass is critical to the operation of the invention. In general, polymeric products result when hydrogenation of a nitrile is carried out in an aqueous system containing ammonia. However, by controlling the amount of water to from about 10% to about 20% by volume of the solvent used, the product is the desired primary amine in high yield. This effect is shown in FIG. 1 where the preferred water range of from about 12% to about 15% is evident. A further advantage of the effect of the specific amount of water in the reaction mass is shown in FIG. 2 where it is seen that the reaction rate is significantly enhanced at a water concentration of about 10%. As seen from this figure, more than 20% of water gives a further slight increase in reaction rate, but the yield of desired product falls off as is evident from FIG. 1. A still further, unexpected advantage of the presence of water in the process is evident from FIG. 3 where the effect of water on catalyst recycling is seen. It is clear from this figure that in an anhydrous system, catalyst efficiency falls off quickly in repeated use. On the other hand, where 12.5% water is present, yields of product remain high when the catalyst is recycled.

In order to further illustrate the invention the following examples are given:

EXAMPLE 1

A stirred autoclave was charged with 400 ml. tetrahydrofuran (THF), 100 ml. ammonia, 50 g. terephthalonitrile (TPN) and 6.0 g. a supported cobalt catalyst and various amounts of water. The autoclave was heated to 120° C. Hydrogen was introduced rapidly until the selected pressure was reached. The absorption of hydrogen started immediately and additonal hydrogen was added to keep the pressure at the selected level. The course of the reaction was monitored by measuring the volume of hydrogen consumed and by periodic withdrawal of a small sample of the reaction mixture for analysis. When the analysis indicated that all of the terephthalonitrile had reacted, the agitation was stopped and the reactor was cooled rapidly and vented. The reaction mixture was filtered to recover the catalyst and then was flash evaporated to remove solvent. The residual oil was flash distilled at about 100° C. and 0.5 mm Hg. to give practically pure primary aromatic amine product (p-xylylene diamine). A small amount of high boiling residue remained in the distillation pot. Results of experiments conducted with various amounts of water and at 1500 and 2500 psig are listed in Table I.

The data in Table I and as plotted in FIG. 1 show that the addition of about 10% of water is beneficial in promoting a higher reaction rate and higher yield of primary amine (distillate). With quantities of water, beyond about 20%, the yield of distillate is reduced.

TABLE I

INFLUENCE OF WATER ON RATE AND SELECTIVITY OF SUPPORTED COBALT CATALYST

Charge: 50 g. TPN, 100 ml. NH$_3$, 400 ml. THF; 3. g (@ 2500 PSI) and 6 g (@ 1500 PSI) of Harshaw 1606 Cobalt Catalyst
Conditions: 115° C. @ 2500 PSI and 120° @ 1500 PSI

| Water % | Reaction time (min) | Rate* (hr.$^{-1}$) | Product Distillate wt. % |
|---|---|---|---|
| Pressure = 2500 psig | | | |
| 0 | 150 | 6.6 | 93.4 |
| 12.5 | 85 | 12 | 96.0 |
| 22 | 90 | 11 | 92.0 |
| 36 | 80 | 12 | 75.8 |
| Pressure = 1500 Psig | | | |
| 0 | 190 | 2.6 | 94.0 |
| 1.5 | 225 | 2.2 | 94.0 |
| 3.1 | 195 | 2.6 | 94.8 |
| 6.3 | 160 | 3.1 | 95.0 |
| 12.6 | 75 | 6.6 | 96.4 |
| 23 | 80 | 6.2 | 91.0 |

*wt. TPN reacted/wt. catalyst - hour

EXAMPLE 2

Catalyst recovered from the experiment of Example 1 in which 12.5% water was used was recharged repeatedly to the autoclave in an otherwise identical procedure carried out at 1500 psig. Parallel experiments were also conducted without the addition of water. The results are summarized in Table II.

The data in Table II show that the yield of distillate product declines rapidly with catalyst reuse in the absence of water. However, with water present, the catalyst can be used repeatedly without substantial change in its performance.

TABLE II

EFFECT OF WATER ON LIFE OF SUPPORTED COBALT CATALYST

| Pass No. | Reaction Time (min) | Relative Rate[c] | Product Yield (%) |
|---|---|---|---|
| No Water[a] | | | |
| 1 | 255 | 0.30 | 93.0 |
| 2 | 170 | 0.48 | n.a.* |
| 3 | 175 | 0.51 | 80.8 |
| 4 | 185 | 0.49 | 79.6 |
| 50 ml. water | | | |
| 1 | 75 | 1.00 | 96.4 |
| 2 | 90 | n.a.* | 96.4 |
| 3 | 110 | n.a.* | 95.4 |
| 4[b] | 105 | 0.91 | 95.4 |
| 5[b] | 100 | 1.00 | n.a.* |

TABLE II-continued
EFFECT OF WATER ON LIFE OF SUPPORTED COBALT CATALYST

| Pass No. | Reaction Time (min) | Relative Rate[c] | Product Yield (%) |
|---|---|---|---|
| 6 | 110 | 1.01 | 93.2 |

[a] Catalyst recovered from pass numbers one thru four weighed 5.6, 5.1, 5.0 and 4.8 g. respectively.
[b] Catalyst recovered from pass numbers three thru five weighed 4.7, 4.4, and 4.0 g., respectively.
[c] Adjusted for catalyst losses noted above.
*n.a. = not available

EXAMPLE 3

Table III illustrates the effect of various solvents in the reaction mass with and without water. As can be seen, water improves the reaction rate with THF, dioxane and xylene, but in the case of xylene the yield of product is very low (54.2%). Furthermore, the addition of water has a deleterious effect in the case of ethanol solvent. Thus, the unexpected specificity of the process is evident.

TABLE III
EFFECT OF WATER AND VARIOUS SOLVENTS ON RATE AND SELECTIVITY

Charge: 50 g. TPN, 6 g. Co catalyst, 100 ml. $NH_3$, 400 ml. diluent
Conditons: 120° C., 1500 psi

| Solvent | Water, % | Time (min.) | Rate w/wh | Product Yield Wt.% |
|---|---|---|---|---|
| Ethanol | 0 | 150 | 3.3 | 87.4 |
| Ethanol | 12.5 | 155 | 3.2 | 72.0 |
| Xylene | 0 | 225 | 2.2 | — |
| Xylene | 12.5 | 85 | 5.8 | 54.2 |
| Dioxane | 0 | 140 | 3.6 | 94.6 |
| Dioxane | 12.5 | 90 | 5.6 | 94.0 |
| THF | 0 | 190 | 2.6 | 94.0 |
| THF | 12.5 | 75 | 6.7 | 96.4 |

EXAMPLE 4

The following Table IV further illustrates the invention and illustrates the use of skeletal type catalysts.

TABLE IV
INFLUENCE OF WATER ON RATE AND SELECTIVITY OF SKELETAL CATALYSTS

Charge: 50 g. TPN; 100 ml. $NH_3$; 400 ml. THF; 5.0 g. catalyst; 50 mls. $H_2O$ as noted.
Conditions: 120° C., 1500 psi

| % $H_2O$ | Rx Time (min.) | Rate (hr.$^{-1}$) | TPN Conv. % (%) | PXDA Selectivity (%) |
|---|---|---|---|---|
| Raney Nickel Catalyst (W. R. Grace #28): | | | | |
| 0 | 210 | 2.9 | 100 | 69.1 |
| 12.5 | 190 | 3.2 | 100 | 96.9 |
| Raney Cobalt Catalyst (W. R. Grace #27): | | | | |
| 0 | 230 | 2.4 | 94 | 40.3 |
| 12.5 | 187.4 | 3.1 | 98 | 89.2 |
| Raney Nickel-Chrominum Promoted Catalyst W. R. Grace #24): | | | | |
| 0 | 136.6 | 4.1 | 95 | 45.9 |
| 12.5 | 168 | 3.5 | 99 | 46.7 |

It will be noted that in the case of both Raney nickel and Raney cobalt both rate and selectivity to p-xylylene diamine (PXDA) are significantly increased when water is present. On the other hand, when a catalyst is used including a metal other than nickel or cobalt (e.g. nickel plus chromium) the benefits obtained by water addition are not significant; e.g. with nickel and chromium as shown above the rate decreased slightly and the increase in specificity was not significant.

The invention claimed is:

1. In the process of hydrogenating aromatic nitriles to primary amines whereby the nitrile is hydrogenated in a solvent system containing added ammonia using a cobalt or nickel catalyst, the improvement of employing as solvent an ether containing four to six carbon atoms and carrying out the hydrogenation in the presence of water in an amount of from about 10% to about 20% by volume of the ether solvent whereby the rate of reaction is increased, secondary amine by-products are reduced and catalyst may be recycled without adverse effects.

2. In the process of hydrogenating aromatic nitriles of the benzene and naphthalene series to primary amines whereby the nitrile is hydrogenated in a solvent system containing added ammonia using a cobalt or nickel catalyst, the improvement of employing a 4 or 5 carbon cyclic ether as solvent and carrying out the hydrogenation in the presence of water in an amount of from about 10% to about 20% by volume of the ether solvent whereby the rate of reaction is increased, secondary amine by-products are reduced and catalyst may be recycled without adverse effects.

3. The process of claim 2 where the nitrile is a member of the benzene series.

4. The process of claim 2 where the ether solvent is tetrahydrofuran.

5. The process of claim 2 where the cyclic ether is dioxane.

6. The process of claim 4 where the nitrile is terephthalonitrile.

7. The process of claim 6 where the range of water is from about 10% to about 15%.

8. The process of claim 7 where the catalyst is supported cobalt or nickel.

9. The process of claim 7 where the catalyst is Raney nickel or Raney cobalt.

* * * * *